(12) United States Patent
Notani et al.

(10) Patent No.: US 10,847,256 B2
(45) Date of Patent: Nov. 24, 2020

(54) SYSTEM AND COMPUTER PROGRAM FOR HEALTHCARE INFORMATION MANAGEMENT IN A MULTI-PARTY HEALTHCARE NETWORK

(71) Applicants: Ranjit Notani, Plano, TX (US); Greg Brady, Dallas, TX (US); Jeff Hook, Coppell, TX (US)

(72) Inventors: Ranjit Notani, Plano, TX (US); Greg Brady, Dallas, TX (US); Jeff Hook, Coppell, TX (US)

( * ) Notice: Subject to any disclaimer, the term of this patent is extended or adjusted under 35 U.S.C. 154(b) by 237 days.

(21) Appl. No.: 15/676,916

(22) Filed: Aug. 14, 2017

(65) Prior Publication Data

US 2018/0046765 A1     Feb. 15, 2018

Related U.S. Application Data

(60) Provisional application No. 62/374,812, filed on Aug. 13, 2016.

(51) Int. Cl.
| | |
|---|---|
| *H04L 9/00* | (2006.01) |
| *G16H 10/60* | (2018.01) |
| *H04L 29/06* | (2006.01) |
| *G06F 21/62* | (2013.01) |
| *G06F 19/00* | (2018.01) |

(52) U.S. Cl.
CPC .......... *G16H 10/60* (2018.01); *G06F 19/321* (2013.01); *G06F 21/6245* (2013.01); *H04L 63/102* (2013.01); *G06F 2221/2141* (2013.01)

(58) Field of Classification Search
CPC ......... G06F 21/6245; G06F 2221/2145; H04L 63/102
See application file for complete search history.

(56) References Cited

U.S. PATENT DOCUMENTS

2015/0213195 A1 *   7/2015   Blechman .............. G16H 10/60
                                                                                            705/51

FOREIGN PATENT DOCUMENTS

WO    WO 2016/077792 A1 *   5/2016   ............. G06F 17/40

* cited by examiner

*Primary Examiner* — Beemnet W Dada
(74) *Attorney, Agent, or Firm* — Karl L. Larson (57) ABSTRACT

A system, computer program product and method for healthcare information management in a multi-party healthcare network. The system includes a plurality of remote computers, a central server, a network interface in communication with the central server and the plurality of remote computers over a network, and a shared database in communication with the central server. The central server is configured to receive patient data for a patient, create an electronic health record for the patient on the shared database of the service provider computer, encrypt the electronic health record, associate a plurality of security permissions with the electronic health record, provide access to the electronic health record to a plurality of remote computers via the multi-party healthcare network based on the relevant security permission for each of the respective plurality of remote computers, receive changes to the patient data for the patient from at least one of the plurality of remote computers, and update the electronic health record for the patient based on the changes to the patient data for the patient. The electronic health record includes the patient data. A single version of the truth exists for the electronic health record for all parties in the multi-party healthcare network.

15 Claims, 8 Drawing Sheets

SYSTEM AND COMPUTER PROGRAM FOR HEALTHCARE INFORMATION MANAGEMENT IN A MULTI-PARTY HEALTHCARE NETWORK

CROSS REFERENCE TO RELATED APPLICATIONS

The present application claims priority to U.S. provisional patent application Ser. No. 62/374,812, entitled "System and Computer Program for Healthcare Information Management in a Multiparty Healthcare Network", filed in the U.S. Patent and Trademark Office on Aug. 13, 2016, having at least one common inventor as the present document and hereby incorporated by reference.

BACKGROUND OF THE INVENTION

Field of the Invention

The present invention is generally related to healthcare information management systems, and more particularly to a system and computer program for healthcare information management in a multi-party healthcare network.

Discussion of the Background

Patient healthcare typically involves multiple healthcare-related providers, supporting organizations, companies and/or entities, including, inter alia, doctors, nurses, technicians, laboratories, specialists, medical imaging facilities, pharmacies, emergency facilities, school and workplace clinics, hospitals, insurance companies, and financial institutions (collectively herein "healthcare entities"). In the prior art, each healthcare entity typically maintained its own separate system. In particular, each healthcare entity typically maintained its own healthcare-related information on its own computer systems, databases and computer programs. Healthcare entities might indirectly communicate with other healthcare entities, such as, for instance, via exchange messages (typically EDI), as needed. For numerous reasons, such separation of patient healthcare-related information on different systems and/or networks is inherently flawed and is not a viable option for creating a multi-party healthcare network, as described herein. For instance, each healthcare entity had to integrate its own internal healthcare information with many other external systems and networks. Further, it resulted in multiple and incomplete versions of the truth with respect to each patient's healthcare-related information.

According to the prior art, each healthcare entity had to potentially integrate their own systems with many if not all of the other healthcare entities in the healthcare network leading to $n^2$ integrations, where 'n' is the number of healthcare entities in the healthcare network. Such an arrangement required additional time and expense in setting up and managing the healthcare network, and was highly coupled. Each healthcare entity in the healthcare network would typically maintain its own systems, including separate computer systems and separate databases. Data related to a particular healthcare entity would typically be stored in separate databases. Computer programs operated on these separate computer systems were required to be maintained by that particular healthcare entity. A large portion of the data contained within the separate databases was typically duplicated data over and over again between each of the computer systems of the separate healthcare entities within the healthcare network. This resulted in an ever-increasing complex web of connections and inter-relationships where there was an attempt to maintain the same data in separate databases and periodically synchronize that data between the separate databases and computer systems within the healthcare network. Further, the data was often stale or out of date between the separate computer systems.

Distributed databases are known in the prior art. A distributed database is a database that is under the control of a central database management system (DBMS) in which storage devices are not all attached to a common CPU. Distributed databases may instead be stored in multiple computers located in the same physical location or may be dispersed over a local area network (LAN) of interconnected computers. For numerous reasons, distributed databases are disjointed and inherently flawed and not viable options for creating a multi-party healthcare network, as described herein. For instance, distributed databases require all participants to use the same database software (often the same version) for each of the participants' respective databases. They also require the database to be directly exposed instead of exposing the application programming interface (API) of the application. Directly exposing the database leads to a high degree of coupling. Any changes to a highly-coupled database typically result in extensive modifications. Further, distributed databases do not have fault tolerance, resulting in issues like "split-brain." Distributed databases also require proximity and may be dispersed over a LAN of interconnected computers, but are not practical to deploy over a wide area network (WAN). As such, distributed databases cannot be easily deployed in a global environment over a WAN. Finally, distributed databases are designed for "synchronous" environments and do not operate well in asynchronous environments.

Thus, there currently exist deficiencies associated with healthcare related systems, and, in particular, with healthcare information management in a multi-party healthcare network.

SUMMARY OF THE INVENTION

Accordingly, one aspect of the present invention is to provide a computer program product embodied on a non-transitory computer readable medium for healthcare information management in a multi-party healthcare network. The healthcare network has shared access to a shared database on a service provider computer over a network. The computer program is implemented by one or more processors executing processor instructions. The computer program product includes (i) a first computer code for receiving patient data for a patient, (ii) a second computer code for creating an electronic health record for the patient on the shared database of the service provider computer, (iii) a third computer code for encrypting the electronic health record, (iv) a fourth computer code for associating a plurality of security permissions with the electronic health record, (v) a fifth computer code for providing access to the electronic health record to a plurality of remote computers via the multi-party healthcare network based on the relevant security permission for each of the respective plurality of remote computers, (vi) a sixth computer code for receiving changes to the patient data for the patient from at least one of the plurality of remote computers, and (vii) a seventh computer code for updating the electronic health record for the patient based on the changes to the patient data for the patient. The electronic health record includes the patient data. A single version of the truth exists for the electronic health record for all parties in the multi-party healthcare network.

Another aspect of the present invention is to provide a system for healthcare information management in a multi-party healthcare network. The system includes a plurality of remote computers, a central server, a network interface in communication with the central server and the plurality of remote computers over a network, and a shared database in communication with the central server. The central server is configured to (i) receive patient data for a patient, (ii) create an electronic health record for the patient on the shared database of the service provider computer, (iii) encrypt the electronic health record, (vi) associate a plurality of security permissions with the electronic health record, (v) provide access to the electronic health record to a plurality of remote computers via the multi-party healthcare network based on the relevant security permission for each of the respective plurality of remote computers, (vi) receive changes to the patient data for the patient from at least one of the plurality of remote computers, and (vii) update the electronic health record for the patient based on the changes to the patient data for the patient. The electronic health record includes the patient data. A single version of the truth exists for the electronic health record for all parties in the multi-party healthcare network.

BRIEF DESCRIPTION OF THE DRAWINGS

A more complete appreciation of the present invention and many of the attendant advantages thereof will be readily obtained as the same becomes better understood by reference to the following detailed description when considered in conjunction with the accompanying drawings, wherein.

DETAILED DESCRIPTION OF THE PREFERRED EMBODIMENTS

Referring now to the drawings, wherein like reference numerals designate identical or corresponding parts throughout the several views, preferred embodiments of the present invention are described.

The present invention provides a computer program and method for healthcare information management in a multi-party healthcare network, as described herein.

The present invention provides a computer program and method for healthcare information management in a multi-party healthcare network that includes support for: capturing, tracking, maintaining and reporting information concerning an individual's electronic health record (EHR). The present invention also provides a platform-as-a-service (PaaS) solution that is a multi-partied, permissions-based security operating platform. It is standards-based and supports all healthcare industry standards including Fast Healthcare Interoperability Resources (FIHR), Health Level-7 (HL7), and Health Insurance Portability and Accountability Act (HIPAA). The present invention provides tracking capabilities relating to individual and core master data for medical, fitness, diet and administrative information.

The present invention provides a patient portal, as well as a native and/or hybrid (native & web-based) mobile solution for both smart phones and tablets. It maintains and manages first-party data and meta-data native to the healthcare network and provides an integration framework consisting of a development environment and tools (SDK) that allow healthcare industry independent software vendors and other third-party applications to easily integrate data and/or workflows with the platform creating an independent network focused on the welfare of the patient versus serving the providers, payers or other related parties.

The present invention, creates, updates and manages, inter alia, the following types of data within an electronic health record (EHR): (i) health and wellness information and data, including patient demographic, fitness and diet information; (ii) results management data, including laboratory test results, radiology procedure results, blood test results, and the like; (iii) order entry & management data, including medication order entry, ancillary services order entry, and the like; (iv) electronic communication and connectivity, including notifications for alerting for medication reminders, pharmacy pick-up availability, abnormal test results, etc.; (v) patient support, such as computer-based patient education, drug recalls, chronic disease management programs, population support group capabilities, and the like; (vi) administrative processes and reporting, including electronic scheduling for hospital admissions, inpatient and outpatient procedures, immediate validation of insurance availability, and the like; and (vii) reporting and population health to the providers, clinicians and payers through the aggregation of the above patient information.

As used herein, an electronic health record (EHR) is, inter alia, a digital version of a patient's paper chart. EHRs are real-time, patient-centered records that make information available instantly and securely to authorized users. While an EHR does contain the medical and treatment histories of patients, an EHR system is built to go beyond standard clinical data collected in a provider's office and can be inclusive of a broader view of a patient's care. EHRs can: (i) contain a patient's medical history, diagnoses, medications, treatment plans, immunization dates, allergies, radiology images, and laboratory and test results; (ii) allow access to evidence-based tools that providers can use to make decisions about a patient's care; and (iii) automate and streamline provider workflow. Using the present invention, a patient's health information can be created and managed by authorized healthcare entities in a digital format capable of being shared with other healthcare entities across more than one healthcare organization and/or network. EHRs are built to share information with other healthcare entities—such as laboratories, specialists, medical imaging facilities, pharmacies, emergency facilities, and school and workplace clinics—so they contain information from all clinicians involved in a patient's care.

Healthcare EHR Manager

Referring to FIGS. 1A-1D, block diagrams illustrating an exemplary multi-party healthcare network in accordance with an embodiment of the present invention, is shown. A healthcare EHR manager utilizes the multi-party healthcare network 100. The non-limiting exemplary multi-party healthcare network 100 includes networked connections to patients 102, healthcare providers 104, supporting companies 106, insurance companies 108, financial institutions 110, and/or external systems 112. Healthcare providers 104 include any healthcare entity engaged in the providing healthcare to patients either directly or indirectly, including without limitation, doctors, hospitals, outpatient clinics, technicians, and laboratories. These healthcare entities collaborate and share information with one another to provide healthcare to one or more patients 102.

Tunable System of Control

The present invention uses a tunable system of control in order to accommodate situations where not all healthcare entities are considered "onboard" (as defined below) the multi-party healthcare network 100. Regarding such, the present invention is configured to work with either all of the healthcare entities onboard the multi-party healthcare network 100 or any portion of the healthcare entities not onboard the multi-party healthcare network 100. Each step in the processing of an EHR may be associated as "onboard" or not. As defined herein, a healthcare entity is considered "onboard" for a step in the processing of an EHR if the multi-party healthcare network 100 is primarily responsible for that particular step in the processing of an EHR. If the multi-party healthcare network 100 is not responsible that particular step in the processing of an EHR, then it is not considered onboard with respect to that particular step. As such, the granularity associated with the tunable system of control is down to the individual step level.

The multi-party healthcare network 100 may be configured to communicate with one or more external systems 112 and/or to link together one or more external systems 112 using the multi-party healthcare network 100 as a bridge between the one or more external systems 112. For example, external systems 112a-112c are shown linked together by multi-party healthcare network 100 in FIG. 1B. According to this example: (i) external system 112a includes one or more insurance companies, one or more patients, and one or more healthcare providers; (ii) external 112b includes one or more healthcare providers and one or more supporting companies; and (ii) external system 112c includes one or more healthcare providers and one or more financial institutions. At least one step in the processing of an EHR for external systems 112a and 112c are considered onboard, and lines 204 and 210 represent data being transmitted from the multi-party healthcare network 100 to external systems 112a and 112c, respectively. At least one step in the processing of an EHR for external system 112b is considered not onboard and line 206 represents data being transmitted to the multi-party healthcare network 100 from external system 112b. Whether a step in the processing of an EHR for external systems 112a-112c is considered onboard is maintained as a configurable state by the present invention. This state may be programmically altered at the flip of a switch for each step in the processing of an EHR for each of the external systems 112a-112c using the software of the present invention. The data would respectively flow in the opposite direction for that particular step as represented respectively by lines 202, 208 and 212. This interaction is shown in more detail in FIGS. 1F and 1G.

Figure 1A:
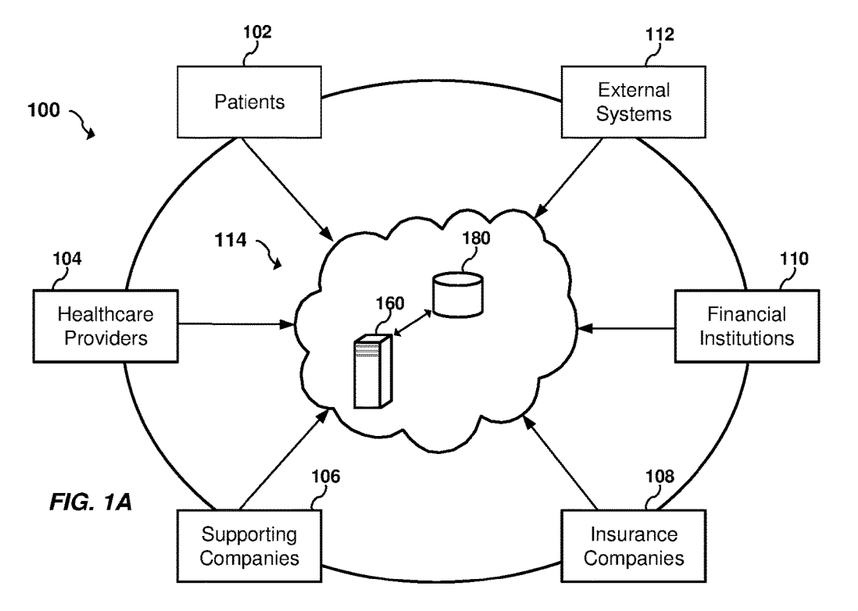
FIGS. 1A-1G are block diagrams illustrating an exemplary multi-party healthcare network in accordance with an embodiment of the present invention.
Figure 1B:
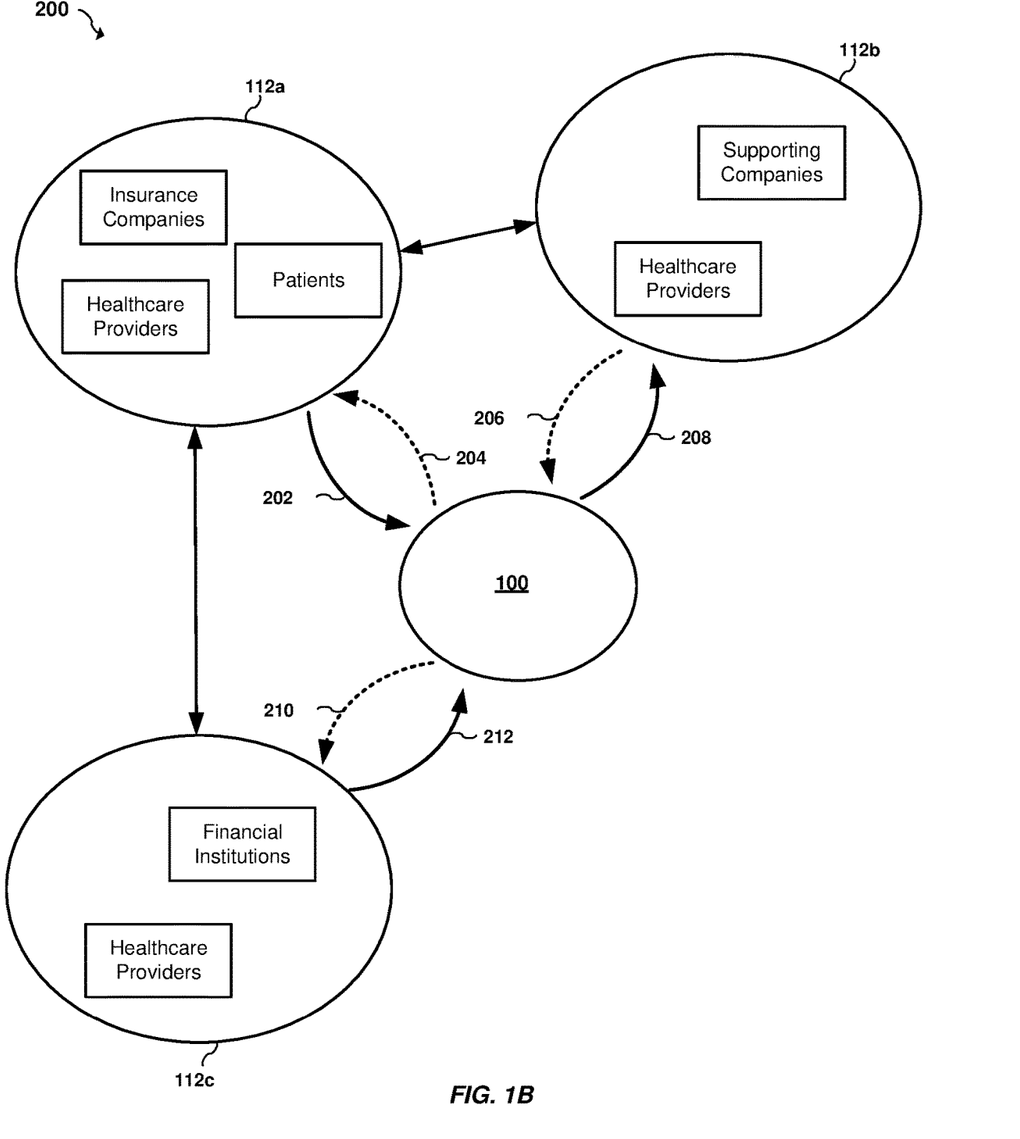
Figure 1C:
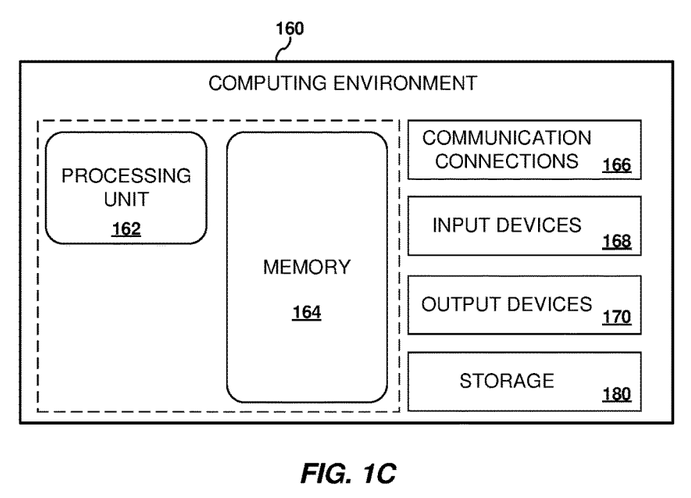
Figure 1D:
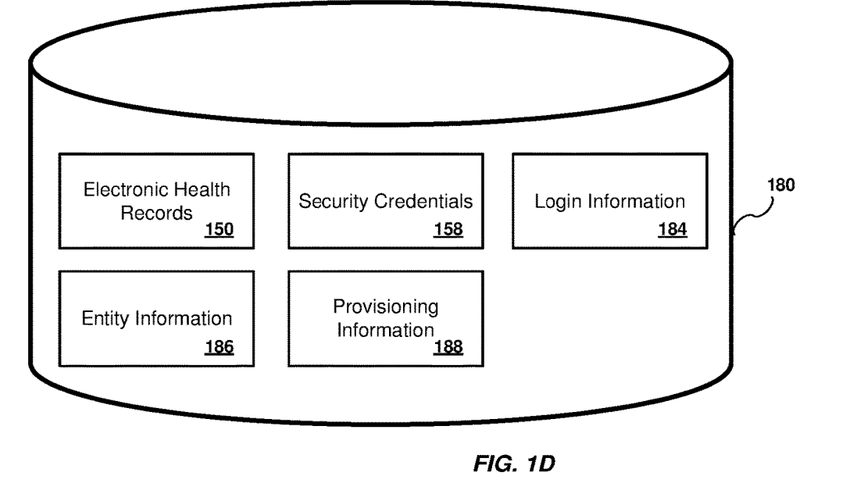
Figure 1E:
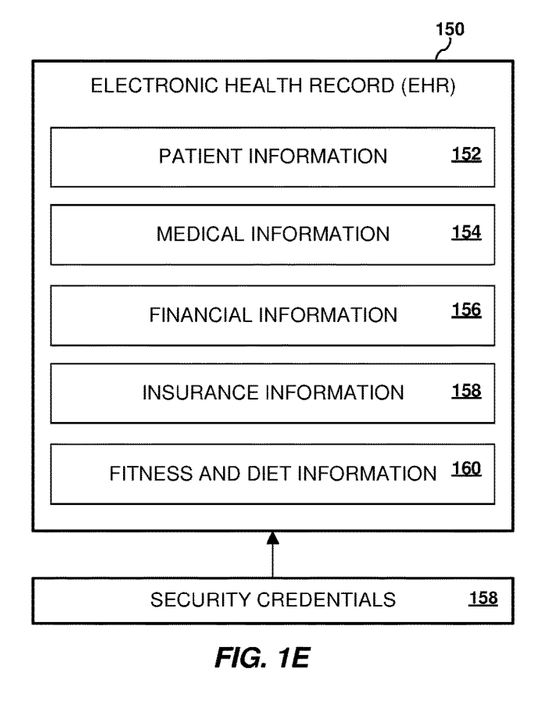
Figure 1F:
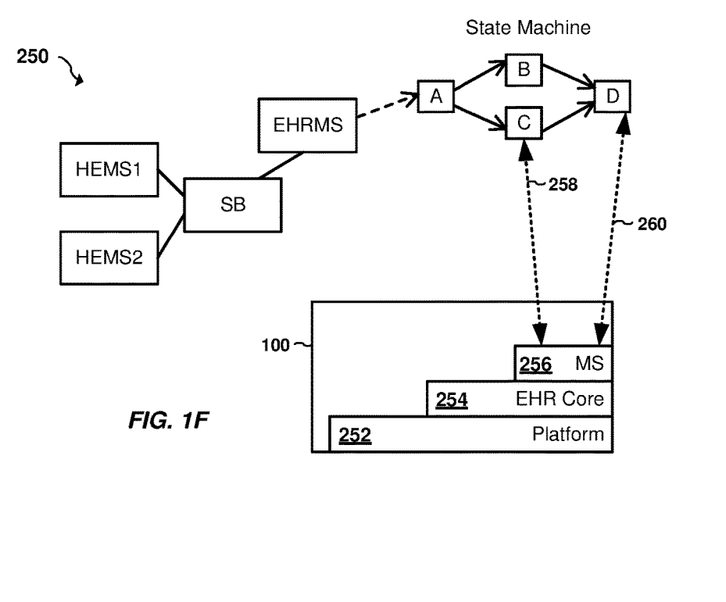

As shown in FIG. 1F, exemplary arrangement 250 includes two exemplary healthcare entity management systems (HEMS1 and HEMS2) that are in communication with a service bus (SB). The service bus (SB) is in communication with an electronic health record management system (EHRMS). Multi-party healthcare network 100 includes management system (MS) 256, electronic health record core (EHR Core) 254 and platform 252. In this example, there are four steps (A-D) and each of these steps may be independently configured to be "onboard" or not. For instance, step A may be configured to be onboard and data is being transmitted to the multi-party healthcare network 100 from an external system, as represented by line 257. Step C may be independently configured to be onboard and data is being transmitted to the multi-party healthcare network 100 from an external system, as represented by line 258. Step D may be independently configured to be not onboard and data is being transmitted from the multi-party healthcare network 100 to an external system, as represented by line 260. At the flip of a switch, either of these data flow may be reversed or stopped. The present invention is configured such that the graphical user interface is automatically adjusted in compliance with the current state of a particular processing step. For instance, a button may be enable or disabled depending on whether a particular processing step is considered onboard or not. Further, entire graphical user interfaces and/or portions thereof may be visible or invisible depending on whether a particular processing step is considering onboard or not.

Figure 1G:
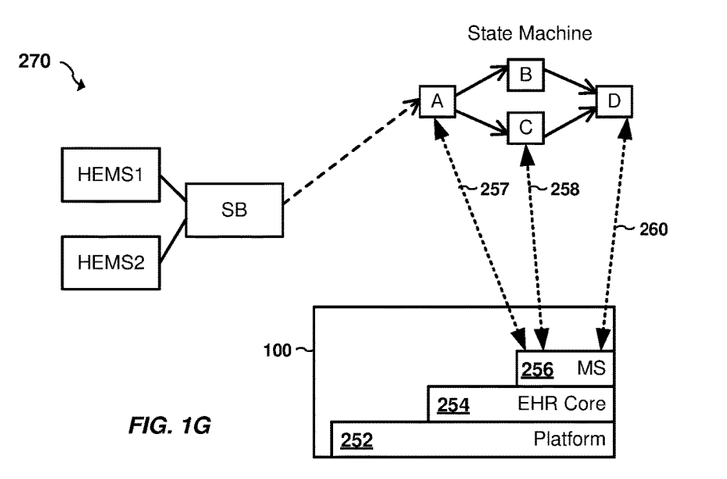

As shown in FIG. 1G, exemplary arrangement 270 includes two exemplary healthcare entity management systems (HEMS1 and HEMS2) that are in communication with a service bus (SB) and there is no health record management system (EHRMS).

Through the multi-party healthcare network 100, the healthcare entities may share healthcare-related data and information, schedule healthcare-related appointments, and generally work together to achieve the common goal of maintaining an EHR for each patient.

The healthcare network management system 114 may include, without limitation, one or more computers/servers 160 in communication with one or more databases 180. The one or more computers/servers 160, and the one or more databases 180, are centralized, but may be connected to the external entities over a network. The computer servers 160 store (e.g., on a computer readable medium and/or one or more databases 180) and execute a healthcare network management program that includes various application tools for management of an EHR, and the like. Data, engines, tables and the like associated with the healthcare network management program may be stored and retrieved, without limitation, in and from, the one or more databases 180.

According to a preferred embodiment, the healthcare entities are linked via a network, such as without limitation the Internet, an Intranet or other communication network. The system includes one or more computers (e.g., computers/servers 160) with one or more processors and one or more computer readable storage mediums, such as without limitation a computer hard-drive, removable drive or memory. One or more computer programs (or engines) having executable instructions may be stored on the computer readable storage medium. For instance, the multi-party healthcare network 100 includes allows the various healthcare entities of the multi-party healthcare network 100 to collaborate with one another and perform certain healthcare-related actions.

According to a preferred embodiment as shown in FIG. 1D, the one or more databases 180 include, without limitation, electronic health record data 150, security credentials data 158, login and user data 184, entity and company data 186, and provisioning data 188. The normal ACID properties of the database are utilized to ensure consistency and atomicity.

Cloud Arrangement

As shown in FIGS. 1A and 1D, one or more databases 180 are maintained by a service provider, such as One Network, in a cloud arrangement. Multiple healthcare entities typically on a single server or several tightly coupled servers all under the control of the service provider. The healthcare entities access the computational resources of the service provider, including, without limitation, one or more databases 180, via a computer network, such as the Internet. This type of arrangement is often referred to as "cloud computing" in that substantially all of the computational resources and databases associated with the multi-party healthcare network 100 is maintained by the service provider which is represented in FIG. 1A as the healthcare network management system 114. Each healthcare entity's computer may contain very little software or data (perhaps a minimal operating system and web browser only), serving as a basic display terminal connected to the Internet to access the service provider. Using the "cloud computing" arrangement of the present invention, each patient and healthcare entity solely within the healthcare network management systems 114 share a single version of truth (SVOT) with respect to the respective data in the database, because they are maintained in the "cloud" by the same service provider. This is significant because a single version of truth was not possible in the prior art because each healthcare entity traditionally maintained its own healthcare-related database(s) locally on its own independent and separate computer system, and, as such, duplicated the data associated with the healthcare-related information resulting in multiple versions of the truth which is often not up to date.

Figure 3A:
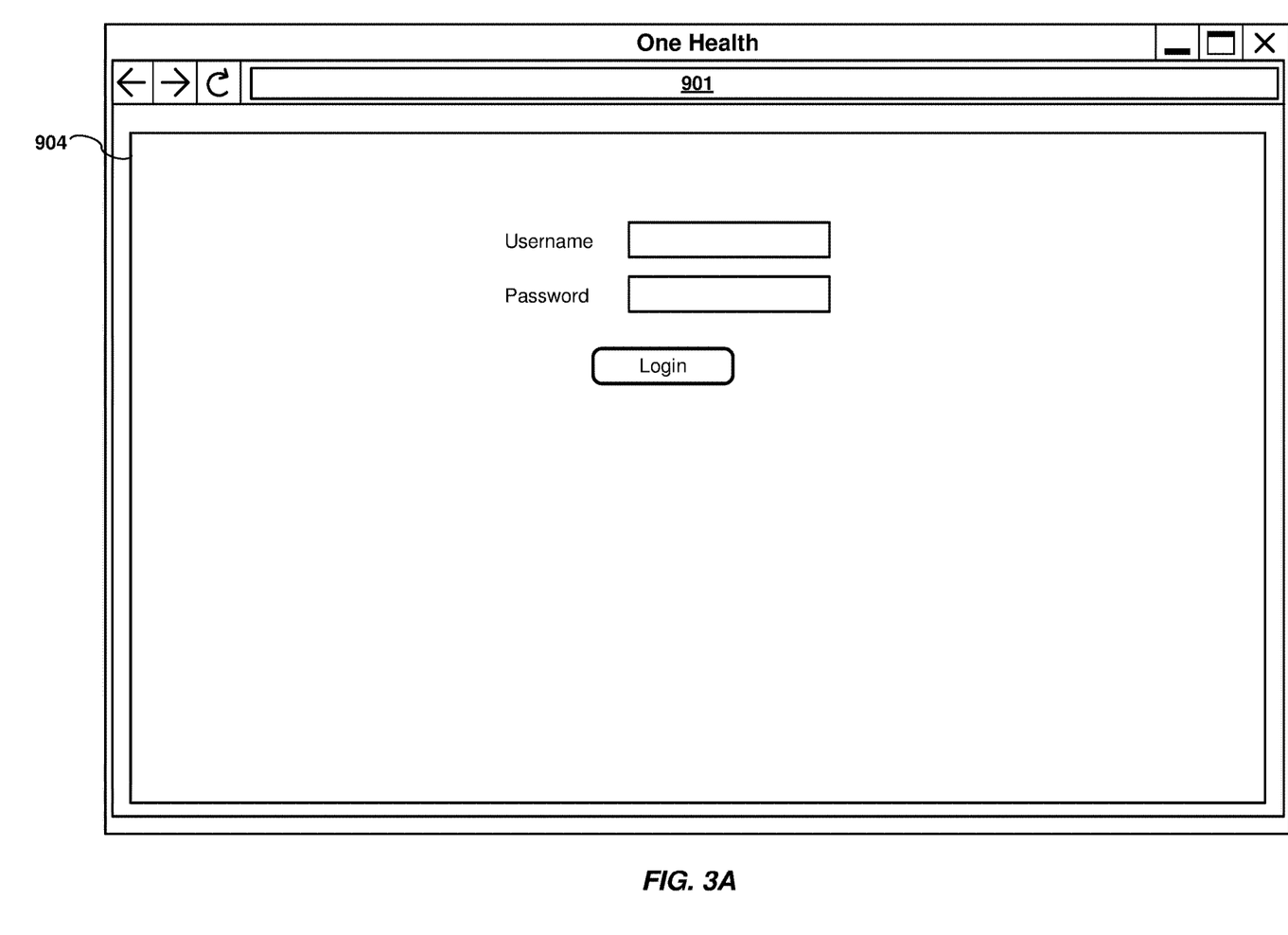
FIG. 3A illustrates portions of a computer-based system in a multi-party healthcare network in accordance with an embodiment of the present invention.

According to the present invention, each patient and healthcare entity logs-in either directly or indirectly with computers/servers 160 or otherwise is in communication with such. For instance, according to one possible non-limiting implementation each patient and healthcare entity logs-in using, without limitation, the graphical user interface shown in FIG. 3A. Alternatively, a patient or healthcare entity may login using a mobile app (not shown). After such log-in or other communication with computers/servers 160, each patient and healthcare entity thereby is provided access to a portion of the patient's electronic health record 150. The electronic health record 150 is shared such that although each patient and healthcare entity may have different views of the patient's electronic health record 150, as noted above, they share a single data element having a single version of truth (SVOT) with respect to the multi-party healthcare network 100 and the electronic health record 150. Each patient and healthcare entity is restricted to the healthcare network and a portion of the electronic health record 150 by the patient's or healthcare entity's allowed permissibility which may be predefined and/or configurable.

As shown in FIG. 1D, one or more databases include one or more tables and/or data including, without limitation, electronic health records 150, security credentials 158, login and user information 184, entity information 186 and provisioning information 188.

Processing Flows

Figure 2A:
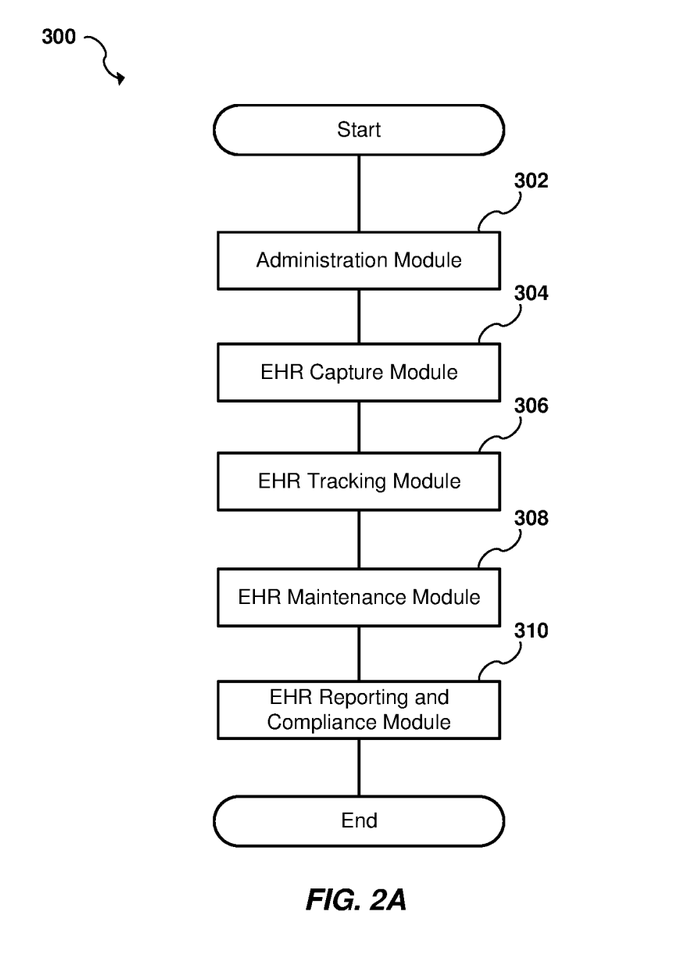
FIGS. 2A-2C are flow charts illustrating a method for healthcare information management in a multi-party healthcare network in accordance with an embodiment of the present invention.

Referring to FIG. 2A, a flow chart illustrating a method for healthcare information management in a multi-party healthcare network 100 in accordance with an embodiment of the present invention are shown. The multi-party healthcare network 100 includes, inter alia, an administrative module 302, an electronic health record (EHR) capture module 304, an EHR tracking module 306, an EHR maintenance module 308, and an EHR reporting and compliance module 310.

As described above, each patient and multiple healthcare entities access the computational resources of a service provider, such as One Network, in a cloud arrangement. Using a computer network, such as the Internet, each patient and healthcare entity logs-in, typically to a single server or several tightly coupled servers all under the control of the service provider in the cloud arrangement, and is provided access to a portion of the patient's electronic health record 150 on database 180. Each patient and healthcare entity share a single version of truth (SVOT) with respect to the respective data in database 180, because they are maintained in the "cloud" by the same service provider. The administrative module 302 is responsible for providing administrative functionality for the multi-party healthcare network 100 using techniques known in the art, including, inter alia, creating new patient and healthcare entity accounts in the cloud arrangement as described herein, and providing permissions and security credentials to the patient healthcare-related data for the respective patients and healthcare entities.

Electronic health record (EHR) capture module 304 includes, inter alia, functionality for automated electronic capture of patient healthcare-related data, including data contained within an electronic health record (EHR) 150, using digital scanning, audio and video translation and conversion into digital readable text, and optical image character recognition. As shown in FIG. 1E, an electronic health record (EHR) 150 includes, inter alia, patient information 152, medical information 154, financial information 156, insurance information 158, and fitness and diet information 160. Patient information 152 contains, inter alia, patient address and billing information, personal information, patient demographics, and the like. Medical information 154 contains, inter alia, patient health information, such as: progress notes, vital signs, medical history, diagnosis information, medications, immunization dates, allergies, radiology images, and lab and test results, and the like. According to at least one embodiment, without limitation, the electronic health record (EHR) 150 is stored in database 180 in an encrypted format. The EHR capture module 304 may communication with one or more I/O devices including, inter alia, scanners, copiers, audio input devices, and video input devices.

EHR tracking module 306 includes, inter alia, functionality for tracking, processing and logging of individual and core master data for medical, fitness, diet and administrative information, including patient healthcare-related actions, to database 180. Healthcare-related actions include, inter alia, scheduled appointments and visits, follow-up activities, and patient payments and other billing information.

EHR maintenance module 308 includes, inter alia, functionality for maintenance of a patient's EHR. EHR reporting and compliance module 310 includes, inter alia, functionality for supporting reporting and compliance requirements under healthcare industry standards.

Figure 2B:
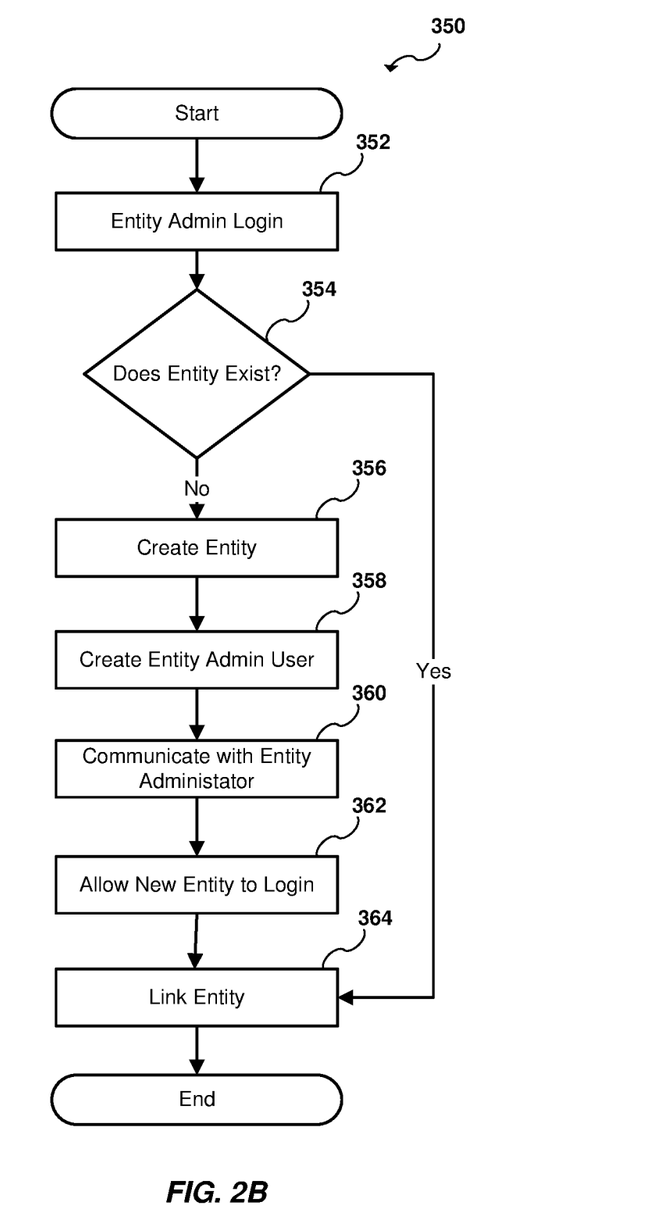

According to at least one embodiment, healthcare entities may be connected within the multi-party healthcare network 100, as needed. For instance, a flow chart illustrating a method for adding entities to a multi-party healthcare network 100 in accordance with an embodiment of the present invention is shown in FIG. 2B. According to this non-limiting example, at block 352, a healthcare entity administrator logs-in either directly or indirectly with computers/servers 160 or otherwise is in communication with such, and requests an affiliation with the multi-party healthcare network 100. A determination is made as to whether that healthcare entity currently exists in the multi-party healthcare network 100 at logic block 354. If the healthcare entity currently exists, then the healthcare entity is linked at block 364.

If the healthcare entity does not currently exist, then the healthcare entity is created at block 356. At block 358, an administrator user is created. The administrator for the new healthcare entity is sent a communication, such as email or the like, and allowed to log-in at blocks 360 and 362, respectively.

Figure 2C:
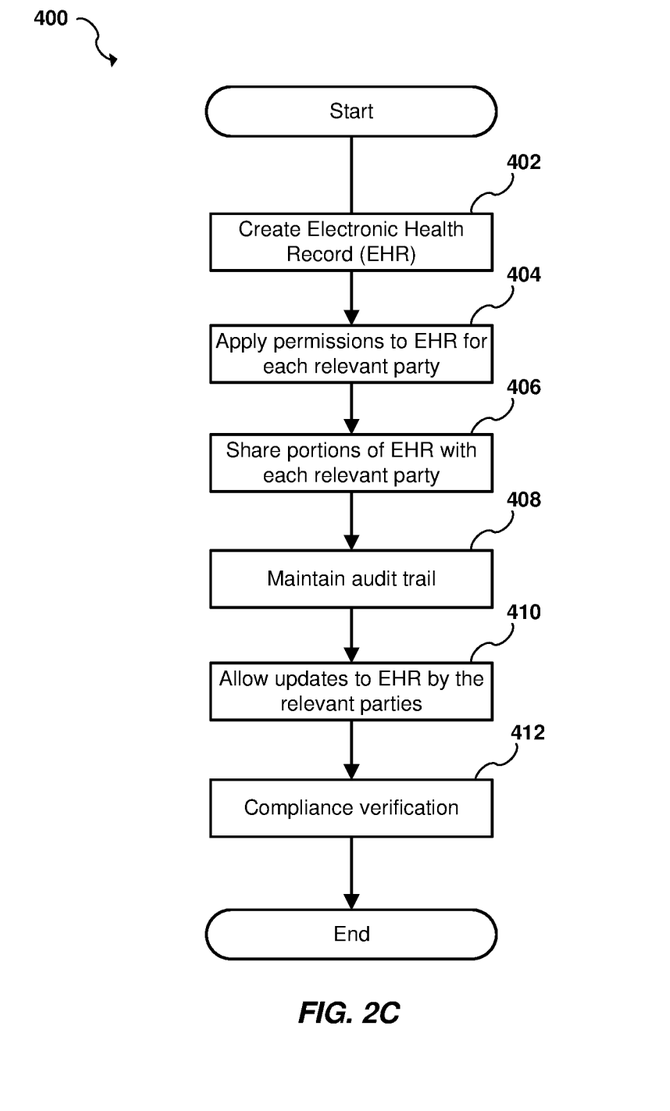

Referring to FIG. 2C, a flow chart illustrating a method for healthcare information management in a multi-party healthcare network 100 in accordance with an embodiment of the present invention are shown. At block 402, a patient is registered within the healthcare network management system 114 and an electronic health record (EHR) 150 is created and stored in a centralized databased 180.

If the patient or healthcare entity do not currently exist, then the patient or healthcare entity is created. If this is a new healthcare entity, then an administrator user is created. The administrator for the new healthcare entity is sent a communication, such as email or the like, and allowed to log-in.

Security permissions for the relevant parties are applied to the electronic health record (EHR) 150 at block 404. Relevant parties may include, inter alia, patients, doctors, medical staff, healthcare-related technicians, hospital and clinic personnel, insurance companies, financial institutions, and the like.

At block 406, appropriate portions of the electronic health record (EHR) 150 are made available to the relevant parties based on their security permissions. An audit trail is stored and maintained at block 408.

At block 410, updates to the electronic health record (EHR) 150 are made available to each of the relevant parties. Interoperability is provided by means of automatic real-time atomic updates of the master electronic health record (EHR) of the patient. Whenever any subscribing application (supporting a primary provider, secondary provider, payer, etc.) updates any subordinate or subset of the patient EHR in one of the networked nodes of a subscribed or subscribing application, an automatic update occurs.

A compliance verification occurs at block 412.

The present invention may utilize one or more computer applications. As used herein, a "computer application" is a computer executable software application of any type that executes processing instructions on a computer or embedded in a processor, and an "application" or "application project" are the files, objects, structures, database resources and other resources used in integrating a computer application into a software platform.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the following claims.

This invention may be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout. As used herein, the term "and/or" includes any and all combinations of one or more of the associated listed items.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As will be appreciated by one of skill in the art, portions of the invention may be embodied as a method, device, or computer program product. Accordingly, portions of the present invention may take the form of an entirely hardware embodiment or an embodiment combining software and hardware aspects all generally referred to as a "circuit" or "module."

The present invention includes a computer program product which may be hosted on a computer-usable storage medium having computer-usable program code embodied in the medium and includes instructions which perform the processes set forth in the present specification. The storage medium can include, but is not limited to, any type of disk including floppy disks, optical disks, CD-ROMs, magneto-optical disks, ROMs, RAMs, EPROMs, EEPROMs, flash memory, magnetic or optical cards, or any type of media suitable for storing electronic instructions.

Computer program code for carrying out operations of the present invention may be written in any programming language including without limitation, object oriented programming languages such as Java®, Smalltalk, C # or C++, conventional procedural programming languages such as the "C" programming language, visually oriented programming environments such as VisualBasic, and the like.

Obviously, many other modifications and variations of the present invention are possible in light of the above teachings. The specific embodiments discussed herein are merely illustrative, and are not meant to limit the scope of the present invention in any manner. It is therefore to be understood that within the scope of the disclosed concept, the invention may be practiced otherwise then as specifically described.

The invention claimed is:

1. A computer program product embodied on a non-transitory computer readable medium for healthcare information management in a multi-party healthcare network, the healthcare network having shared access to a shared database on a service provider computer over a network, wherein the computer program is implemented by one or more processors executing processor instructions, the computer program product comprising:
   a first computer code for receiving patient data for a patient from a one or more of a plurality of remote computers in communication with respectively one or more of a plurality of remote parties;
   a second computer code for creating an electronic health record for the patient on the shared database of the service provider computer, wherein the electronic health record includes the patient data, and wherein a single version of the truth exists without duplication for the electronic health record for all parties in the multi-party healthcare network;
   a third computer code for encrypting the electronic health record;

a fourth computer code for associating a plurality of security permissions with the electronic health record;

a fifth computer code for providing access to the electronic health record to one or more of the plurality of remote computers via the multi-party healthcare network based on the relevant security permission for each of the respective plurality of remote computers, wherein each of the plurality of remote parties are associated with on an onboard or non-onboard state within the multi-party healthcare network;

a sixth computer code for receiving changes to the patient data for the patient from at least one of the plurality of remote computers;

a seventh computer code for updating the electronic health record for the patient based on the changes to the patient data for the patient;

an eighth computer code for managing the data flow of patient data received from, or accessed by, the plurality of remote computers in which the respective plurality of remote parties to the multi-party healthcare network have either an onboard or non-onboard state; and a ninth computer code for managing and programmatically altering the onboard or non-onboard state associated with one or more of the plurality of remote parties.

2. The computer program product of claim 1, wherein the service provider computer is a cloud computer.

3. The computer program product of claim 2, wherein the healthcare network is primarily responsible for the processing of the electronic health record.

4. The computer program product of claim 2, wherein the healthcare network is not primarily responsible for the processing of the electronic health record.

5. The computer program product of claim 4, wherein the computer program product further comprises a tenth computer code for providing access to the electronic health record to one or more external systems, wherein the healthcare network is configured as a bridge between the electronic health record and the one or more external systems.

6. The computer program product of claim 2, wherein the computer program product further comprises a tenth computer code for tracking changes to the electronic health record.

7. The computer program product of claim 6, wherein the computer program product further comprises an eleventh computer code for reporting changes to the electronic health record.

8. The computer program product of claim 2, wherein access to the service provider computer is provided as a platform-as-a-service (PasS).

9. The computer program product of claim 2, wherein the electronic health record complies with at least one selected from the group consisting of FIHR, HL7, and HIPPA standards.

10. The computer program product of claim 2, wherein one or more of the plurality of remote computers is a smart phone or tablet computer.

11. The computer program product of claim 2, wherein one or more of the plurality of remote computers are in communication with at least one selected from the group consisting of doctors, nurses, technicians, laboratories, specialists, medical imaging facilities, pharmacies, emergency facilities, school and workplace clinics, hospitals, insurance companies, and financial institutions.

12. The computer program product of claim 2, wherein the computer program product further comprises an eighth computer code for providing an integration framework to the plurality of remote computers, wherein the integration framework includes a development environment and tools that allow one or more third-party applications to integrate data or workflows with the computer program product.

13. The computer program product of claim 2, wherein the electronic health record includes patient information, medical information, financial information, insurance information, and fitness and diet information.

14. The computer program product of claim 2, wherein the patient data includes at least one selected from the group consisting of patient medical history data, patient diagnosis data, patient medication data, patent treatment plan data, patient immunization data, patient allergy data, patient radiology image data, patient laboratory data, and patient test data.

15. A system for healthcare information management in a multi-party healthcare network, the system comprising:

a plurality of remote computers in communication with respectively a plurality of remote parties;

a central server;

a network interface in communication with the central server and the plurality of remote computers over a network;

a shared database in communication with the central server;

wherein the central server is configured to:

receive patient data for a patient from a one or more of the plurality of remote computers in communication with respectively one or more of the plurality of remote parties;

create an electronic health record for the patient on the shared database of the service provider computer, wherein the electronic health record includes the patient data, and wherein a single version of the truth exists without duplication for the electronic health record for all parties in the multi-party healthcare network;

encrypt the electronic health record;

associate a plurality of security permissions with the electronic health record;

provide access to the electronic health record to one or more of the plurality of remote computers via the multi-party healthcare network based on the relevant security permission for each of the respective plurality of remote computers, wherein each of the plurality of remote parties are associated with on an onboard or non-onboard state within the multi-party healthcare network;

receive changes to the patient data for the patient from at least one of the plurality of remote computers;

update the electronic health record for the patient based on the changes to the patient data for the patient;

manage the data flow of patient data received from, or accessed by, the plurality of remote computers in which the respective plurality of remote parties to the multi-party healthcare network have either an onboard or non-onboard state; and manage and programmatically alter the onboard or non-onboard state associated with one or more of the plurality of remote parties.

* * * * *